(12) United States Patent
Harman et al.

(10) Patent No.: US 7,842,283 B2
(45) Date of Patent: *Nov. 30, 2010

(54) GENERATION OF THERAPEUTIC MICROFOAM

(75) Inventors: Anthony David Harman, Henley-on-Thames (GB); Paul Harper, Buckinghamshire (GB); Neil Pollock, Hertfordshire (GB); Gary Stewart Sinclair, Suffolk (GB)

(73) Assignee: BTG International Limited, London (GB)

( * ) Notice: Subject to any disclaimer, the term of this patent is extended or adjusted under 35 U.S.C. 154(b) by 324 days.

This patent is subject to a terminal disclaimer.

(21) Appl. No.: 11/580,059

(22) Filed: Oct. 13, 2006

(65) Prior Publication Data

US 2007/0031346 A1 Feb. 8, 2007

Related U.S. Application Data

(62) Division of application No. 10/432,328, filed as application No. PCT/GB01/05186 on Nov. 23, 2001.

(30) Foreign Application Priority Data

Nov. 24, 2000 (GB) .................. 0028692.2

(51) Int. Cl.

| A61K 9/12 | (2006.01) |
|---|---|
| B65D 81/32 | (2006.01) |
| B65D 83/14 | (2006.01) |
| A61M 11/00 | (2006.01) |
| A61K 9/00 | (2006.01) |
| A61K 9/08 | (2006.01) |
| A61J 1/05 | (2006.01) |
| A61J 3/00 | (2006.01) |
| A61P 9/14 | (2006.01) |
| B05B 7/32 | (2006.01) |

(52) U.S. Cl. ................ 424/45; 424/400; 128/200.23; 222/635; 239/337; 514/945

(58) Field of Classification Search ...................... None
See application file for complete search history.

(56) References Cited

U.S. PATENT DOCUMENTS 2,630,183 A 3/1953 Foutz
2,724,383 A 11/1955 Lockhart (Continued)

FOREIGN PATENT DOCUMENTS

DE 3050812 C2 3/1985

(Continued)

OTHER PUBLICATIONS

U.S. Appl. No. 10/513,911, filed Nov. 2004, Harman et al.*

(Continued)

*Primary Examiner*—Yvonne L Eyler
*Assistant Examiner*—Christopher R Lea
(74) *Attorney, Agent, or Firm*—Finnegan, Henderson, Farabow, Garrett & Dunner, L.L.P.

(57) ABSTRACT

A method for producing a microfoam suitable for use in scleropathy of blood vessels comprises introducing a physiologically acceptable blood-dispersible gas into a container (1) holding an aqueous sclerosant liquid and releasing the mixture of blood-dispersible gas and sclerosant liquid, whereby upon release of the mixture the components of the mixture interact to form a microfoam.

18 Claims, 5 Drawing Sheets

U.S. PATENT DOCUMENTS

| | | | |
|---|---|---|---|
| 3,698,453 | A | 10/1972 | Morane et al. |
| 3,767,085 | A | 10/1973 | Cannon et al. |
| 3,897,672 | A | 8/1975 | Scheindel |
| 3,955,720 | A | 5/1976 | Malone et al. |
| 3,970,219 | A | 7/1976 | Spitzer et al. |
| 4,019,657 | A | 4/1977 | Spitzer et al. |
| 4,040,420 | A | 8/1977 | Speer |
| 4,127,131 | A | 11/1978 | Vaillancourt |
| 4,276,885 | A | 7/1981 | Tickner et al. |
| 4,292,972 | A | 10/1981 | Pawelchak et al. |
| 4,466,442 | A | 8/1984 | Hilmann et al. |
| 4,538,920 | A | 9/1985 | Drake |
| 4,589,452 | A | 5/1986 | Clanet |
| 4,718,433 | A | 1/1988 | Feinstein |
| 5,048,750 | A | 9/1991 | Tobler et al. |
| 5,064,103 | A | 11/1991 | Bennett |
| 5,071,379 | A | 12/1991 | Poizot |
| 5,084,011 | A | 1/1992 | Grady |
| 5,141,738 | A | 8/1992 | Rasor et al. |
| 5,425,366 | A | 6/1995 | Reinhardt et al. |
| 5,425,580 | A | 6/1995 | Beller |
| 5,454,805 | A | 10/1995 | Brony |
| 5,542,935 | A | 8/1996 | Unger et al. |
| 5,556,610 | A | 9/1996 | Yan et al. |
| 5,623,085 | A | 4/1997 | Gebhard et al. |
| 5,656,200 | A | 8/1997 | Boettcher et al. |
| 5,676,962 | A | 10/1997 | Cabrera Garrido et al. |
| 5,733,572 | A | 3/1998 | Unger et al. |
| 5,902,225 | A | 5/1999 | Monson |
| 6,053,364 | A | 4/2000 | van der Heijden |
| 6,536,629 | B2 | 3/2003 | van der Heijden |
| 6,561,237 | B1 | 5/2003 | Brass et al. |
| 6,572,873 | B1 | 6/2003 | Osman et al. |
| 6,942,165 | B1 * | 9/2005 | Osman et al. ............... 239/337 |
| RE38,919 | E | 12/2005 | Garrido et al. |
| 7,025,290 | B2 * | 4/2006 | Osman et al. ............... 239/337 |
| 7,357,336 | B2 | 4/2008 | Osman et al. |
| 2002/0031476 | A1 | 3/2002 | Trevino et al. |
| 2002/0077589 | A1 | 6/2002 | Tessari |
| 2002/0101785 | A1 | 8/2002 | Edwards et al. |
| 2004/0101480 | A1 | 5/2004 | Osman et al. |
| 2004/0156915 | A1 | 8/2004 | Harman et al. |
| 2006/0049269 | A1 | 3/2006 | Osman et al. |
| 2006/0062736 | A1 | 3/2006 | Wright et al. |
| 2006/0280690 | A1 | 12/2006 | Wright et al. |
| 2007/0003488 | A1 | 1/2007 | Wright et al. |
| 2007/0003489 | A1 | 1/2007 | Wright et al. |
| 2007/0031345 | A1 | 2/2007 | Harman et al. |
| 2007/0031346 | A1 | 2/2007 | Harman et al. |
| 2007/0104651 | A1 | 5/2007 | Wright et al. |
| 2008/0145401 | A1 | 6/2008 | Osman et al. |
| 2008/0274060 | A1 | 11/2008 | Wright et al. |

FOREIGN PATENT DOCUMENTS

| | | |
|---|---|---|
| DE | 8704600 | 11/1987 |
| DE | 3417182 | 1/1989 |
| EP | 0 011 381 | 5/1980 |
| EP | 0217582 | 4/1987 |
| EP | 0324938 | 7/1989 |
| EP | 0 564 505 | 10/1993 |
| EP | 0 613 836 | 9/1994 |
| EP | 0656203 | 6/1995 |
| EP | 0997396 | 5/2000 |
| FR | 2 672 038 | 7/1992 |
| FR | 2 775 436 | 9/1999 |
| GB | 2369996 | 6/2002 |
| JP | H10-81895 | 10/1998 |
| WO | WO 92 05806 | 4/1992 |
| WO | WO 94/21384 | 9/1994 |
| WO | WO 95/00120 | 1/1995 |
| WO | WO 96/08227 | 3/1996 |
| WO | WO 96 25194 | 8/1996 |
| WO | WO 97/13585 | 4/1997 |
| WO | WO 99 43371 | 9/1999 |
| WO | WO 00 24649 | 5/2000 |
| WO | WO 00/72821 | 7/2000 |
| WO | WO 2005/048976 | 7/2000 |
| WO | WO 00 66274 | 11/2000 |
| WO | WO 00 72821 | 12/2000 |
| WO | WO 00/78629 | 12/2000 |
| WO | WO 02/058834 | 8/2002 |
| WO | WO 2004/047969 | 6/2004 |
| WO | WO 00/48984 | 6/2005 |
| WO | WO 2005/048977 | 6/2005 |
| WO | WO 2005/0489883 | 6/2005 |

OTHER PUBLICATIONS

U.S. Appl. No. 10/522,529, filed Jan. 2005, Wright et al.*
U.S. Appl. No. 10/890,267, filed Jul. 2004, Harman et al.*
"Newer aspects of the technique of treating varicosities", K. Sigg, 1949, *Therapeutische Umschau*, 6, 127-134 and a translation into English.
"Non-operative retrograde phlebosclerosation with Varsyl foam", P. Flückiger, 1956, *Schweizerische Medizinische Wochenschrift* [Swiss Medical Weekly] 48, 1368-1370 and a translation into English.
"Angiology. On the aetilogy and treatment of varices of the lower extremities", H. Mayer, H. Brücke, 1957, *Chirurgische Praxis* [Surgical Practice] 4, 521-528 and a translation into English.
"Sclerosing agents—toxicity and mechanism of action", Z. Salamon, 1973, *Wiadomosci Lekarskie*, 26 (19), 1819-1822 and a translation into English.
"Venous sclerosis with foam 'Foam Medical Systems'", J. Garcia Mingo, Revista Española de Medicina y Círugla Cosmética, 7, 29-31.
German Nullity Action Complaint filed Jun. 27, 2007 and translation into English.
German Nullity Action First Brief filed Dec. 3, 2001 and translation into English.
German Nullity Action Supplemental Brief filed Dec. 31, 2002 and translation into English.
German Nullity Action Kreusler Brief filed Jan. 27, 2003 and translation into English.
German Nullity Action Decision by German Court in English dated Feb. 4, 2003.
German Nullity Action English Translation of the Substantiation of Appeal to the Federal Court of Justice on Sep. 26, 2003.
German Nullity Action English Translation of the Reply to appeal dated Feb. 12, 2004.
European Patent Office Opposition to EP 1 337 238 on behalf of Chemische Fabrik Kreussler & Co. GmbH, dated Dec. 10, 2007.
Affidavit for Submission to the European Patent Office by Lorenzo Tesseri for the presentation of "LA Sclero Mousse" at the meeting of the French Society of Phlebology in Paris on Dec. 11, 1999.
Content of lecture titled "La Sclero Mousse" given to the 23rd Meeting of the European Phlebectomy Society in Brussels on Apr. 1, 2000, pp. 10-13.
Frullini, "New Technique in Producing Sclerosing Foam in a Disposable Syringe," Dermatol Surg 2000; 26: 705-706.
Tessari, "Nouvelle Technique d'Obtention de la Scléro -Mousse," Phlebologie 2000; 53; No. 1, p. 129.
A. Cavezzi, "The Use of Sclerosant Foam in Sclerotherapy: possibilities and limits", Management of Venous Disease in the New Millennium, pp. 16-17, Jul. 2000.
A. Frullini et al., "Sclerosing Foam in the Treatment of Varicose Veins and Telangiectases: History and Analysis of Safety and Complications", Dermatol Surg. vol. 28, No. 1, pp. 11-15, Jan. 2002.
Frullini, A "Foam Sclerotherapy: a review" Phlebolymphology, No. 40, p. 125-129, 2003.
English translation of Opposition to the European Patent EP 1 180 015 B1, filed Sep. 21, 2006.
Nullity Appellant's statement dated Apr. 4, 2007 in German Nullity Appeal Proceedings BTG International Ltd., 114-59/03.

Judgment dated May 22, 2007, in German Nullity Appeal Proceedings BTG International Ltd., X ZR 56/03.

Tessari, L., "The Tourbillon Turbulence," In Foam Sclerotherapy State of the Art, ed. J.P. Heneriet, editions Phlébologique Francais pp. 51-55 (2002).

Office Action dated Nov. 14, 2008 for U.S. Appl. No. 10/536,862.

Frullini, A., "New Technique in Producing Sclerosing Foam in a Disposable Syringe," Dermatol Surg 26:7:Jul. 2000, pp. 705-706.

* cited by examiner

GENERATION OF THERAPEUTIC MICROFOAM

This application is a Divisional of application Ser. No. 10/432,328, filed Apr. 2, 2004, which is a national stage application under 35 U.S.C. § 371(c) of International Application No. PCT/GB01/05186, filed internationally on Nov. 23, 2001, which claims the benefit of priority to GB Application No. 0028692.2, filed in the United Kingdom on Nov. 24, 2000, the entire disclosures of which are incorporated herein by reference.

The present invention relates to a method and apparatus for the generation of microfoam comprising a sclerosing material, particularly a sclerosing liquid, which is suitable for use in the treatment of various medical conditions involving blood vessels, particularly varicose veins and other disorders involving venous malformation.

Sclerosis of varicose veins is based on the injection into the veins of liquid sclerosant substances which, by inter alia causing a localised inflammatory reaction, favour the elimination of these abnormal veins. When a sclerosing substance is injected in liquid form, it is mixed with the blood contained in the vein and is diluted in an unknown proportion. The results are uncertain, owing to over-dosage or under-dosage, and are limited to short varicose segments. As the size of the varicose veins to be injected decreases, this dilution is less and the results obtained are more predictable.

Until recently, sclerosis was a technique selected in cases of small and medium varicose veins, those with diameters equal to or greater than 7 mm being treated by surgery. Sclerosis and surgery complemented one another but sclerosis treatment continued not to be applicable to large varicose veins. In these large varicose veins, if a sclerosing substance was injected, its concentration in the vein, its homogeneous distribution in the blood, and the time for which it is in contact with the internal walls of the vessel treated were not known.

In 1946, Orbach injected a few cubic centimeters of air into small varicose veins and confirmed a displacement of the blood inside the vessel which was occupied by the injected air. A sclerosing solution introduced immediately afterwards was more effective than if it had been injected into the blood. However, in thick varicose veins, when air is injected the phenomenon described of the displacement of the blood by the injected air does not occur but the air forms a bubble inside the vein which makes the method ineffective in these vessels.

The same author had the idea, a few years later, of injecting foam obtained by agitation of a container containing sodium tetradecyl sulfate, which is an anionic sclerosing detergent with a good foaming capability. The method was of little use owing to the large size of the bubbles formed and was dangerous owing to the side effects of atmospheric nitrogen which is only slightly soluble in blood. Both methods had limited practical repercussion being used only in small varicose veins.

WO-A-00/66274 (Garcia) discloses a device for producing foamed sclerosing agent, preferably for treating varices, which includes a container in which the sclerosing liquid is deposited and a connection means to a propellant gas source. The device is hermetically closed by a head piece into Which a small diameter probe tube is inserted to reduce the pressure. The tube extends inside the container, which is also closed by a valve whose actuation causes the escape of the foamed sclerosing agent via an outlet nozzle in the head piece. However, no information is given on how the device works. There is no disclosure of a microfoam by Garcia An injectable microfoam suitable for therapeutic uses has now been developed and is described in EP-A-0656203 and U.S. Pat. No. 5,676,962 (incorporated herein by reference). These patents describe a microfoam produced with a sclerosing substance which, when injected into a vein, displaces blood and ensures that the sclerosing agent contacts the endothelium of the vessel in a known concentration and for a controllable time, achieving sclerosis of the entire segment occupied.

The advantages of use of this foam are that it allows the concentration of the sclerosing agent in the blood vessel to be known, since the microfoam displaces the blood and is not diluted therein in to the same extent as a simple liquid would be. Furthermore it allows homogeneous distribution of the sclerosis product in the vein to be ensured and the time for which it is kept in contact with the internal walls of the vein to be controlled. None of which factors is known precisely or is controllable with the use of sclerosing agents in simple liquid form.

The preparation of such a microfoam may be carried out with a solution of any sclerosing substance, particularly polidocanol, alkali metal tetradecyl sulfate e.g. sodium salt, hypertonic glucose or gluco-saline solutions, chromic glycerol, ethanolamine oleate, sodium morrhuate or iodic solutions.

However, this known method requires production of microfoam by the physician, pharmacist or an assistant immediately prior to administration to the patient. Such procedure allows for variation of agent depending upon the person preparing it, with content of gas, bubble size and stability all needing attention with respect to the condition being treated. It also requires a high degree of care and knowledge that may be difficult to replicate under pressure, i.e. when time available to prepare the foam is short.

A solution to this problem is offered in co-pending application WO 00/72821-A1 (BTG International Limited), incorporated herein by reference. This further addresses the perception that large volumes of nitrogen should not unnecessarily be introduced into patients, particularly where large vessels are being filled with foam and eliminated, which is a problem when using air as the gas for producing the foam. Gas embolism with high levels of nitrogen or other insoluble gases remains a possibility.

The solubility of physiological gases in aqueous fluids, such as blood, varies considerably. Thus while nitrogen is almost twice as insoluble in water as oxygen at STP, carbon dioxide is over fifty times as soluble in aqueous liquids as nitrogen and over twenty five times as soluble as oxygen.

One form of device that could potentially provide the desired properties would be an aerosol dispenser of a type that produces foams. However, for the purposes of generating a microfoam to be injected into a human or animal body, it is undesirable to have a liquefied propellant gas of the type usually employed in aerosol canisters, e.g. such as butane. This determines that the gas from which the foam is to be made must itself be pressurised to allow production of foam.

Bubbler devices have been used in accessories for use with 'environmentally friendly' aerosol devices that operate using air under low pressure, i.e. hand pump conditions. Two such devices are supplied by Airspray International as the 'Airspray™ Finger Pump Foamer' and 'Airspray™ Mini-Foamer'. The former is said to be suitable for simple water based formulations while the latter is suggested for cosmetics, hair or skin care preparations. A second such device is provided as an optional extra in the Swedspray/Eurospray™ hand pump device as a foaming nozzle. This device is marketed as being suitable for use to 'make you own cleansing foam or shaving lather'.

The inventors in co-pending application WO 00/72821-A1 found that use of the available hand-pump devices, which in any case are not sterile, cannot produce good microfoam owing to outgassing with high loadings of carbon dioxide, nor with inclusion of significant amounts of glycerol which otherwise stabilises microfoam. Furthermore, when significant back-pressure is applied to the outlet of such device, such as when attached to a syringe to be loaded for injecting the foam, stuttering occurs. Use of low ejection velocity with this device can cause wetting at the nozzle which results in large bubbles caused by air entrapment. In any case the foams so produced, whether with oxygen or carbon dioxide, tend to be low-density polyhedral in nature, with a tendency to break up on passage down a hypodermic needle.

The inventors in co-pending application WO 00/72821-A1 have solved this by providing a method and device that are capable of producing a uniform injectable microfoam made with a relatively low concentration of a sclerosing agent and a significant amount of a blood dispersible gas in sterile fashion without volatile liquid propellants or the need for the operator to directly be concerned in control of its parameters. The method comprises passing a mixture of a physiologically acceptable blood dispersible gas and an aqueous sclerosant liquid through one or more passages having at least one cross-sectional dimension of from 0.1 to 30 µm, the ratio of gas to liquid being controlled such that a microfoam is produced having a density of between 0.07 g/ml to 0.19 g/ml and a half-life of at least 2 minutes.

A preferred form of gas in co-pending application WO 00/72821-A1 comprises 50% vol/vol or more oxygen, the remainder being carbon dioxide, or carbon dioxide, nitrogen and trace gases in the proportion found in atmospheric air. Preferably the sclerosing agent is a solution of polidocanol or sodium tetradecylsulfate in an aqueous carrier, e.g. water, particularly in a saline.

However, the present inventors have now identified a potential problem with this formulation. Up to now, there have been no reports of the instability of polidocanol when stored in the presence of oxygen, but the inventors have observed that polidocanol could slowly decompose in the presence of oxygen. Thus it appears to be undesirable to store polidocanol in a pressurised can in the presence of oxygen, for example as taught in co-pending application WO 00/72821-A1, as it may result in a reduced shelf life.

For the purpose of this application terms have the following definitions. Physiologically acceptable blood dispersible gas is a gas that is capable of being substantially completely dissolved in or absorbed by blood. A sclerosant liquid is a liquid that is capable of sclerosing blood vessels when injected into the vessel lumen. Scleropathy or sclerotherapy relates to the treatment of blood vessels to eliminate them. An aerosol is a dispersion of liquid in gas. A major proportion of a gas is over 50% volume/volume. A minor proportion of a gas is under 50% volume/volume. A minor amount of one liquid in another liquid is under 50% of the total volume. Half-life of a microfoam is the time taken for half the liquid in the microfoam to revert to unfoamed liquid phase.

In a first aspect of the present invention there is provided a method for producing a microfoam suitable for use in scleropathy of blood vessels, particularly veins, characterised in that it comprises introducing a physiologically acceptable blood-dispersible gas into a container holding an aqueous sclerosant liquid and releasing the mixture of blood-dispersible gas and sclerosant liquid, whereby upon release of the mixture the components of the mixture interact to form a microfoam.

The mixture of blood-dispersible gas and sclerosant liquid is preferably pressurised to a pre-determined level. Preferred pressures are in the range 800 mbar to 4.5 bar gauge (1.8 mbar to 5.5 bar absolute). Pressures in the range of 1 bar to 2.5 bar gauge have been found to be particularly effective—at these pressures, there is very little change in either the density or the half-life of the resulting foam.

The source of blood-dispersible gas may remain in place while the foam is being dispensed. However, preferably the source of the blood-dispersible gas is removed before the mixture of blood-dispersible gas and sclerosant liquid is released, having pressurised the mixture to a pre-determined level. Thus the blood-dispersible gas may be introduced through the same orifice or lumen as is used for the dispensing of the mixture of blood-dispersible gas and sclerosant liquid. Foaming occurs upon release of the mixture through this orifice or lumen.

Alternatively, the blood-dispersible gas may be introduced through an orifice or lumen remote from that used for the dispensing of the mixture of blood-dispersible gas and sclerosant liquid, for example in the bottom of the container holding the aqueous sclerosant liquid. In this case there would be no need to remove the source of blood-dispersible gas place while the foam is being dispensed.

The sclerosant liquid may be stored at atmospheric pressure (or just above) before the blood-dispersible gas is introduced. This has the advantage that no ingress of non-sterile air can occur prior to introduction of the gas. The sclerosant liquid may be stored in the presence of an inert gas or mixture of inert gases. "Inert gas", as used in this specification, refers to one which is unlikely to react with the sclerosant liquid so as to change its chemical nature. Suitable inert gases include carbon dioxide, helium, neon, argon, and especially nitrogen.

Alternatively, the sclerosant liquid may be stored at sub-atmospheric pressure, thus minimising the amount of nitrogen in the final pressurised gas mix and also keeping unreactive carbon dioxide which is soluble in the foam to a minimum level in the final pressurised gas mix. Preferred storage pressures are in the range 0.3 bar to 0.7 bar absolute (−0.7 bar to −0.3 bar gauge). Storage pressures in the range of 0.4 bar to 0.6 bar absolute, especially 0.5 bar absolute, have been found to be particularly effective.

The container holding the aqueous sclerosant liquid would normally be made to a particular pressure specification. Typically aluminium cans have a 12 bar burst pressure. Such cans are liable to implode during handling if a pressure lower than 0.3 bar absolute is used. Once implosion has occurred, the cans may not function correctly, and the resultant crimping may cause a microhole to be produced.

On the other hand, using a higher pressure level once the mixture of blood-dispersible gas and sclerosant liquid has been pressurised renders sub-atmospheric pressures unnecessary.

The invention allows the physiologically acceptable blood-dispersible gas to be introduced into the container holding the aqueous sclerosant liquid immediately before the mixture of blood-dispersible gas and sclerosant liquid is released. This would conveniently be performed on the same day as the foam is to be used in scleropathy of blood vessels, or within a twenty-four period prior to the foam being so used. The foam does not have to be used immediately, however; moreover, if the container holding the aqueous sclerosant liquid is inadvertently shaken while the blood-dispersible gas is introduced, it can be desirable to leave it for five or so minutes to allow the contents to settle. Thus the formation of an undesirable macrofoam is avoided.

A device such as the 'Airspray™ Finger Pump Foamer' and 'Airspray™ Mini-Foamer', described above, could be used to pressurise the container. However, preferably the blood-dispersible gas is stored in a container provided with engaging means for the container holding the aqueous sclerosant liquid. The engaging means may be made integral with the containers, or may comprise an intermediate element. Part of this intermediate element may optionally be removed before the mixture of blood-dispersible gas and sclerosant liquid is released, having pressurised the mixture to a pre-determined level. The intermediate element may include a foaming element to allow the components of the mixture to interact to form a microfoam. The foaming element may take any form, and generally comprises one or more passages of small cross-sectional dimension, as discussed below.

After the blood-dispersible gas has been introduced, the mixture is preferably passed through one or more passages having at least one cross-sectional dimension of from 0.1 to 30 μm, the ratio of gas to liquid being controlled such that a microfoam is produced having a density of between 0.07 g/ml to 0.19 g/ml and a half-life of at least 2 minutes.

Preferably the microfoam is such that 50% or more by number of its gas bubbles of 25 μm diameter and over are no more than 200 μm diameter.

Preferably the gas/liquid ratio in the mix is controlled such that the density of the microfoam is 0.09 g/ml to 0.16 g/ml, more preferably 0.10 g/ml to 0.15 g/ml.

Preferably the microfoam has a half-life of at least 2.5 minutes, more preferably at least 3 minutes. The half-life may be as high as 1 or 2 hours or more, but is preferably less than 60 minutes, more preferably less than 15 minutes and most preferably less than 10 minutes.

Half-life is conveniently measured by filling vessel with a known volume and weight of foam and allowing liquid from this to drain into a graduated vessel, the amount drained in a given time allowing calculation of half-life i.e. of conversion of microfoam back into its component liquid and gas phases. This is preferably carried out at standard temperature and pressure, but in practice ambient clinic or laboratory conditions will suffice.

The ratio of gas to liquid used in the final mixture is important in order to control the structure of the microfoam produced such that its stability is optimised for the procedure and the circumstances in which it is being carried out. For optimum foams it is preferred to mix 1 volume of sclerosant liquid with from approximately 4 to 10 volumes (STP), more preferably 6 to 8 volumes (STP), of gas.

A further preferred form of gas in the final mixture comprises 60% vol/vol or more oxygen, the remainder being carbon dioxide and nitrogen. One preferred final gas mixture is 60 to 90% vol/vol oxygen and 5 to 40% vol/vol carbon dioxide and 3 to 10% vol/vol nitrogen. Such a mixture may be made by introducing a physiologically acceptable blood-dispersible gas comprising 95%-100% vol/vol oxygen into a container holding an aqueous sclerosant liquid stored under an gas mix of mainly carbon dioxide with a small amount of nitrogen, in the ratio 75:25 or greater.

A preferred composition for the final gas mixture is 81% vol/vol oxygen, 13% vol/vol carbon dioxide and 6% vol/vol nitrogen. Such a final gas mixture may be made by introducing oxygen at an initial pressure of 5-6 bar absolute from a 300 ml container into a similar 300 ml container holding an aqueous sclerosant liquid stored under an reduced pressure inert gas atmosphere of 0.5 bar absolute, such inert gas atmosphere comprising a mix of 75% vol/vol carbon dioxide and 25% vol/vol nitrogen, until pressure equilibrium is reached between the two containers.

The carbon dioxide would be expected to dissolve to some extent in the sclerosant liquid. The above figures refer to the proportions of carbon dioxide on the assumption that no dissolving has occurred.

It is found that passing a stream of the sclerosant liquid and the gas under pressure through one or more passages of 0.1 μm to 30 μm as described provides a stable blood-dispersible-gas-based sclerosant injectable microfoam that was previously thought to be only producible by supply of high amounts of energy using high speed brushes and blenders.

Preferably the sclerosing agent is a solution of polidocanol or sodium tetradecylsulfate in an aqueous carrier, e.g. water, particularly in a saline. More preferably the solution is from 0.25 to 5% v/v polidocanol, preferably in sterile water or a physiologically acceptable saline, e.g. in 0.5 to 2% v/v saline. Concentration of sclerosant in the solution will be advantageously increased for certain abnormalities such as Klippel-Trenaunay syndrome.

The sclerosant may also contain additional components, such as stabilising agents, e.g. foam stabilising agents, e.g. such as glycerol. Further components may include alcohols such as ethanol. Even though this can reduce foam stability, it is thought to solubilise low-molecular-weight oligomers of polidocanol.

Most preferably the concentration of sclerosant in the aqueous liquid is a 0.25-2% vol/vol solution, preferably of polidocanol, in water or saline. The water or saline also, in some cases at least, preferably contain 2-5% vol/vol physiologically acceptable alcohol, e.g. ethanol. The polidocanol solution is preferably phosphate buffered. The pH of the buffer is preferably adjusted to be physiological, e.g. from pH 6 to pH 8. In the presence of dissolved carbon dioxide, the value would be expected to be around pH 6.8.

Suitable pressures before the mixture of blood-dispersible gas and sclerosant liquid is released are typically in the range 0.01 to 9 bar over atmosphere. For use of meshes, e.g. one to eight meshes arranged in series, having apertures of 10-30 μm diameter, 0.8 to 4.5 atmospheres over bar will, inter alia, be suitable. For use of three to five meshes of 20 μm aperture it is found that 1.5-1.7 bar over atmospheric is sufficient to produce a good foam. A pressure of 2-2.5 bar over atmospheric may advantageously be used. For a 1 μm pore size membrane, a pressure of 5 bar or more over atmospheric pressure is preferred.

In one preferred form of the invention the passages are in the form of a membrane, e.g. of polymer such as polytetrafluoroethylene, wherein the membrane is formed of randomly connected fibres and has a rated effective pore size which may be many times smaller than its apparent pore size. A particularly suitable form of this is a biaxially oriented PTFE film provided by Tetratec™ USA under the trade mark Tetratex™, standard ratings being 0.1 to 10 μm porosity. Preferred pore sizes for the present method and devices are 3 to 7 μm. This material may be laminated with a porous backing material to give it strength and has the advantage that one or two such meshes may be sufficient to produce a foam that meets the use requirements set out above with regard to stability.

In a second aspect of the present invention there is provided a device for producing a microfoam suitable for use in scleropathy of blood vessels, particularly veins, comprising a housing in which is situated a pressurisable chamber containing a solution of the sclerosing agent in a physiologically acceptable solvent referred to in the first aspect; a pathway with one or more outlet orifices by which the solution may pass from the pressurisable chamber to the exterior of the device through said one or more outlet orifices and a mechanism by which the pathway from the chamber to the exterior can be opened or closed such that, when the container is pressurised and the pathway is open, fluid will be forced along the pathway and through the one or more outlet orifices;

said housing incorporating an inlet for the admission of a pressurised source of physiologically acceptable gas that is dispersible in blood; the gas being in contact with the solution on activation of the mechanism such as to produce a gas-solution mixture;

said pathway to the exterior of the housing including one or more foaming elements;

characterised in that the blood-dispersible gas is stored in a container provided with engaging means for the housing holding the aqueous sclerosant liquid.

The foaming element(s) may comprise one or more passages of cross sectional dimension, preferably diameter, 0.1 μm to 30 μm, through which the solution and gas mixture is passed to reach the exterior of the device, said passing of said mixture through the passages forming a microfoam of from 0.07 to 0.19 g/ml density and of half-life at least 2 minutes.

The source of blood-dispersible gas may remain in place while the foam is being dispensed. However, preferably the source of the blood-dispersible gas is removed before the mixture of blood-dispersible gas and sclerosant liquid is released, having pressurised the mixture to a pre-determined level. Thus the inlet for the admission of physiologically acceptable gas may be the outlet used for dispensing of the mixture of blood-dispersible gas and sclerosant liquid.

The engaging means may be made integral with the containers, or may comprise an intermediate element. Part of this intermediate element may optionally be removable before the mixture of blood-dispersible gas and sclerosant liquid is released, having pressurised the mixture to a pre-determined level. The intermediate element may include a foaming, element to allow the components of the mixture to interact to form a microfoam.

The engaging means may comprise a connector which engages at one end with the container for the aqueous sclerosant liquid and at the other end with the container for the blood-dispersible gas. The ends may be at any angle, but to ensure that the apparatus is held in the correct position when the blood-dispersible gas is introduced the ends are preferably parallel to each other. Most conveniently the connector comprises a generally cylindrical element with open ends.

The connector may take any form which allow the containers to be pushed together for the introduction of the blood-dispersible gas and for them to be separated again. Thus it may include a snap mechanism for the rapid pushing together of the containers, or a screw thread for their slower pushing together. However, preferably the connector includes a cam track, whereby rotation of the containers relative to each other moves them together in a controlled fashion. The cam track may be further provided with a release track, so that the containers may be separated again. One or more detents may be provided in the cam track, to enable the user to gauge the progress of the introduction of the blood-dispersible gas.

A removable spacer may be provided to prevent the containers from being pushed together until required. Preferably this takes the form of an annular collar positioned in between a connector in two parts. One part of the connector is equipped with an engaging pin and the other with the cam track.

An additional removable sleeve may be provided sealing the connector before use. This may take the form of a tamper-evident shrink wrapped sleeve of thin plastics material positioned over the removable spacer.

The two parts of the connector may be separated after the introduction of the blood-dispersible gas. Preferably the connector includes an aerosol valve actuator mechanism, whereby separation leaves the actuator mechanism attached to the container for the sclerosing agent. Preferably the connector includes an aerosol valve actuator in position on the container holding the aqueous sclerosant liquid. The foaming element may be made integral with the aerosol valve actuator mechanism.

The connector may engage with the mounting cup flanges of the two containers, such as the guide sleeve disclosed in EP-A-0 217 582 (Unilever PLC et al.). Alternatively, it may be provided with a male element, such as pin, which engages with a female element, such as a plug, made integral with the containers.

Either inside the pressurisable chamber disposed in the pathway to the valve, or on the downstream side of the valve, is provided an element having the one or more passages described in the first aspect mounted such that the gas liquid mixture, i.e. dispersion of bubbles in liquid, aerosol or macrofoam, passes through the passage or passages and is caused to foam. This element may conveniently be located in a cap on the canister in between the valve mounting and an outlet nozzle. Conveniently, depression of the cap operates the valve. Alternatively the element is within the canister mounted above the gas liquid interface.

The gas pressure employed will be dependent upon materials being used and their configuration, but conveniently will be 0.01 to 9 bar over atmospheric, more preferably 0.1-3 bar over atmospheric, and still more preferably 1.5-2.5 bar over atmospheric pressure.

The blood-dispersible gas is stored in a container provided with engaging means for the housing holding the aqueous sclerosant liquid. The engaging means may be made integral with the containers, or may comprise an intermediate element. Part of this intermediate element may optionally be removable before the mixture of blood-dispersible gas and sclerosant liquid is released, having pressurised the mixture to a pre-determined level. The intermediate element may include a foaming element to allow the components of the mixture to interact to form a microfoam.

Preferred forms of the one or more elements defining the multiple passages for use in the device of the present invention are meshes, screens or sinters. Thus one or more meshes or perforated screens or sinters will be provided, with some preferred forms employing a series of such elements arranged in parallel with their major surfaces perpendicular to the path of solution/gas expulsion.

It is preferred that any elements in the devices according to the invention which have a critical dimension, and which are likely to be exposed to an aqueous solution for more than a few minutes, are made of a material that does not change dimension when exposed to aqueous material. Thus such elements preferably should not be of a water-swellable material such as Nylon 66, but of a polyolefin such as polypropylene or polyethylene. On the other hand, Nylon 66 is ideal for elements where exposure to aqueous solution is so short that swelling is unlikely, such as the element defining the passages of 0.1 μm-30 μm dimension.

Preferably the canister is sized such that it contains sufficient gas and solution to form up to 500 ml of microfoam, more preferably from 1 ml up to 200 ml and most preferably from 10 to 60 ml of microfoam. Particularly the amount of gas under pressure in such canisters should be sufficient to produce enough foam to treat, i.e. fill, at least one varicosed human saphenous vein. The most preferred canister device is disposable after use, or cannot be reused once opened such as to avoid problems of maintaining sterility.

In a third aspect of the present invention there is provided a device for producing a microfoam suitable for use in scleropathy of blood vessels, in the form of a kit comprising:
(a) a housing in which is situated a pressurisable chamber containing a solution of the sclerosing agent in a physiologically acceptable solvent; a pathway with one or more outlet orifices by which the solution may pass from the pressurisable chamber to the exterior of the device through said one or more outlet orifices and a mechanism by which the pathway from the chamber to the exterior can be opened or closed such that, when the container is pressurised and the pathway is open, fluid will be forced along the pathway and through the one or more outlet orifices; and
(b) a pressurised container containing a physiologically acceptable blood-dispersible gas;

said housing incorporating an inlet for the admission of blood-dispersible gas; the gas being in contact with the solution on activation of the mechanism such as to produce a gas-solution mixture.

The pathway to the exterior of the housing may include one or more foaming elements.

The housing in which is situated the pressurisable chamber containing the solution of the sclerosing agent and the container containing the blood-dispersible gas are preferably placed in a sealed package, or otherwise sold as a single unit. This would normally be intended for a single treatment, and discarded after use.

The sclerosant liquid may be stored in the presence of an inert gas or mixture of inert gases, as discussed above.

In a fourth aspect of the present invention there is provided a device for producing a microfoam suitable for use in scleropathy of blood vessels, particularly veins, comprising a housing in which is situated a pressurisable chamber containing a solution of the sclerosing agent in a physiologically acceptable solvent referred to in the first aspect; a pathway with one or more outlet orifices by which the solution may pass from the pressurisable chamber to the exterior of the device through said one or more outlet orifices and a mechanism by which the pathway from the chamber to the exterior can be opened or closed such that, when the container is pressurised and the pathway is open, fluid will be forced along the pathway and through the one or more outlet orifices;

said housing incorporating an inlet for the admission of a pressurised source of physiologically acceptable gas that is dispersible in blood; the gas being in contact with the solution on activation of the mechanism such as to produce a gas-solution mixture;

said pathway to the exterior of the housing including one or more foaming elements;

characterised in that the blood-dispersible gas is stored in the presence of an inert gas or mixture of inert gases.

The present invention will now be described further by way of illustration only by reference to the following Figures and Examples. Further embodiments falling within the scope of the invention will occur to those skilled in the art in the light of these. These include those disclosed in EP-A-0 217 582 (Unilever PLC et al.) and EP-A-0 997 396 (Kurt Vogelsang GmbH).

FIGURES

FIG. 2 shows an exploded view of a canister device of the second aspect incorporating a variant of the cam track mechanism of FIG. 1, as further described in Example 2 below, in which

FIG. 3 shows an exploded view of a canister device of the second aspect incorporating a screw thread mechanism, as further described in Example 3 below, in which

FIG. 4 shows an exploded view of a canister device of the second aspect incorporating a snap mechanism, as further described in Example 4 below, in which FIG. 4a and FIG. 4b shows the connector in open and closed position, FIG. 4c shows the complete assembly, FIG. 4d shows a cut-away portion of the connector.

FIG. 5 is a view of the secure actuator of FIGS. 2, 3 and 4, in which

EXAMPLES

Example 1

Figure 1:
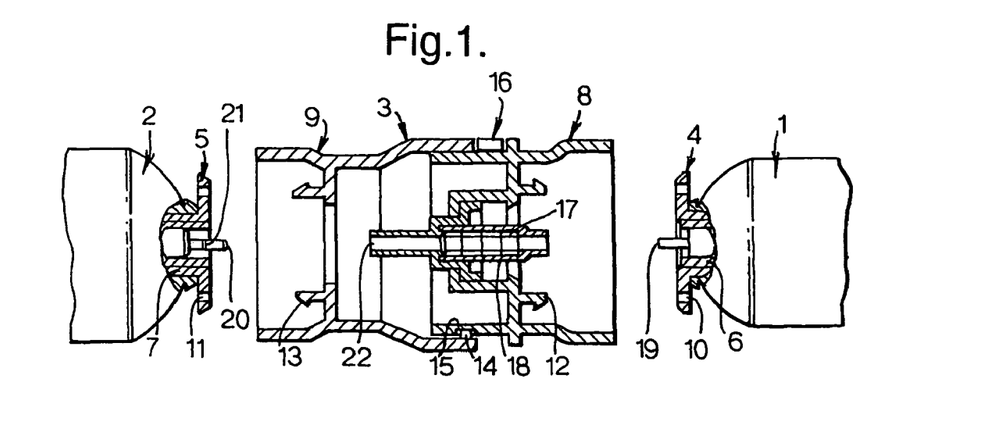
FIG. 1 shows a cross-sectional view of a device of the second aspect of the invention incorporating a cam track mechanism, as further described in Example 1 below.

FIG. 1 illustrates a device of the second aspect of the invention incorporating a cam track mechanism. The device comprises a container (1) for an aqueous sclerosant liquid, a container (2) for a physiologically acceptable blood-dispersible gas and an engaging means comprising a connector (3).

The device is designed to be used with the container (1) for the aqueous sclerosant liquid charged with 18 ml of a polidocanol formulation, comprising 1% polidocanol in a pH 7.3 phosphate-buffered aqueous solution including a small proportion of ethanol to solubilise the polidocanol, and a mixture of 75% $CO_2$/25% $N_2$ gas at 0.5 bar absolute pressure. The aerosol valve on the can continuously meters a specified mix ratio of liquid to gas to create a foam of specified density.

The container (2) for a physiologically acceptable blood-dispersible gas is charged with pure oxygen gas at 5.8 bar absolute pressure. It is used to pressurise the container (1) for the aqueous sclerosant liquid just before the microfoam is required, and is then discarded. The reason for adding the oxygen at the last moment before use is that polidocanol appears incompatible with long term exposure to pressurised oxygen.

The two containers will thus be referred to hereinafter as the PD [polidocanol] can (1) and the $O_2$ can (2).

The connector assembly (3) between the two cans allows one-time sterile transfer of oxygen from the $O_2$ can (2) to the PD can (1) when actuated by a user. This action produces a pressurised gas mix in the PD can (1) at 3.15±0.15 bar absolute pressure when the sterile gas transfer is completed.

Each of the cans (1, 2) is provided with a snap-fit mounting (4, 5). These may be made as identical mouldings. The snap-fit parts (4, 5) engage the crimped-on mounting cup (6, 7) of each can (1, 2) with high frictional force. The connector is made in two halves (8, 9), and the high frictional force allows the user to grip the two connected cans (1, 2) and rotate the connector halves (8, 9) relative to each other without slippage between connector (3) and cans. Each of these can mountings (6, 7) has snap-fit holes (10, 11) for engaging mating prongs (12, 13) which are on the appropriate surfaces of the two halves (8, 9) of the connector.

The connector (3) is an assembly comprising a number of injection mouldings. The two halves (8, 9) of the connector are in the form of cam track sleeves which fit together as two concentric tubes. These tubes are linked by proud pins (14) on one half that engage sunken cam tracks (15) on the other half. The cam tracks have three detented stop positions. The first of these detents is the stop position for storage. An extra security on this detent is given by placing a removable collar (16) in a gap between the end of one sleeve and the other. Until this collar (16) is removed it is not possible to rotate the sleeves past the first detent position. This ensures against accidental actuation of the connector.

A further element of security is given by providing a tamper-evident label across the join between the cam track sleeve (9) and the removable collar (16).

The cam track sleeves (8, 9) are injection moulded from ABS as separate items, and are later assembled so that they engage one another on the first stop of the detented cam track. The assembled sleeves are snap-fitted as a unit onto the $O_2$ can (2) mounting plate (5) via four locating prongs. The security collar and tamper-evident label are added at this point to make an $O_2$ can subassembly.

The connector (3) includes in its interior a mesh stack shuttle (17) on the connector half (8) adjacent to the PD can (1). The mesh stack shuttle (17) is comprised of four injection moulded disk filters with mesh hole size of 20 microns and an open area of approx. 10%. These are pre-assembled within a casing tube (18). The end fittings of the stack (17) are designed to give gas-tight face and/or rim seals against the stem valves (19, 20) of the two cans (1, 2) to ensure sterility of gas transfer between the two cans.

The mesh stack shuttle (17) is assembled onto the PD can valve (19) by push-fitting the components together in a sterile environment.

The PD can (1) and attached shuttle (17) are offered up to the connector (3) and the attached $O_2$ can (2), and a sliding fit made to allow snap-fitting of the four locating prongs (12) on the PD can side of the connector (3) into the mating holes (10) in the mounting plate (4) on the PD can (1). This completes the assembly of the system. In this state, there is around 2 mm of clearance between the stem valve (20) of the $O_2$ can (2) and the point at which it will form a seal against a female luer outlet from the stack.

When the tamper-evident sleeve and security collar (16) are removed, it is possible to grasp the two cans (1, 2) and rotate one half of the connector (3) against the other half to engage and open the $O_2$ can valve (20).

As the rotation of the connector (3) continues to its second detent position, the PD can valve (19) opens fully. The gas flow from the $O_2$ can (2) is restricted by a small outlet hole (21) in the stem valve (20). It takes about 30 seconds at the second detent position for the gas pressure to (almost) equilibrate between the two cans to a level of 3.15 bar±0.15 bar.

After the 30 second wait at the second detent position, the connector (3) is rotated further to the third detent position by the user. At this position, the two cans (1, 2) can be separated, leaving the PD can (1) with half (8) of the connector and the shuttle assembly (17) captive between the connector and the PD can. The $O_2$ can (2) is discarded at this point.

It is important to keep the PD can (1) vertical and not to shake the contents, as this would form a macrofoam in the can and disturb the specified mixing ratio of gas to liquid and hence the microfoam density. However, if the PD can (1) is inadvertently shaken while the gas is introduced, it can be left for five or so minutes to allow the contents to settle. Thus the undesirable macrofoam is eliminated. Even if the can is not inadvertently shaken, it is desirable to wait two to three minutes for the macrofoam formed from the gassing operation to collapse.

Each canister (1, 2) is of standard 200 to 350 ml design with an aluminium wall, the inside surface of which is coated with an epoxy resin resistant to action of polidocanol and oxygen (e.g. Hoba 7940, Holden UK). The bottom of the PD can (1) is domed inward. The dome provides a perimeter area around the bottom of the inner chamber in which a level of polidocanol solution is retained sufficient for the bottom open end of a dip tube to be submerged therein when the top of the dome is no longer covered with the solution. In this manner, by use of indicia on the outside of the canister to indicate the position of the dip tube, the canister can be oriented to extract the last fraction of solution if desired. In practice a vertical orientation is sufficient.

A standard 1" diameter aerosol valve (19) (Precision Valves, Peterborough, UK) is crimped into the top of the PD can (1) before or after sterile filing with the solution and is activatable by depressing the mesh stack shuttle (17), which functions as an aerosol valve actuator mechanism, to release the contents via an outlet nozzle (22) sized to engage a luer fitting of a syringe or multi-way connector (not shown).

Example 2

Figures 2A, 2B, 2C, 2D, 2E:
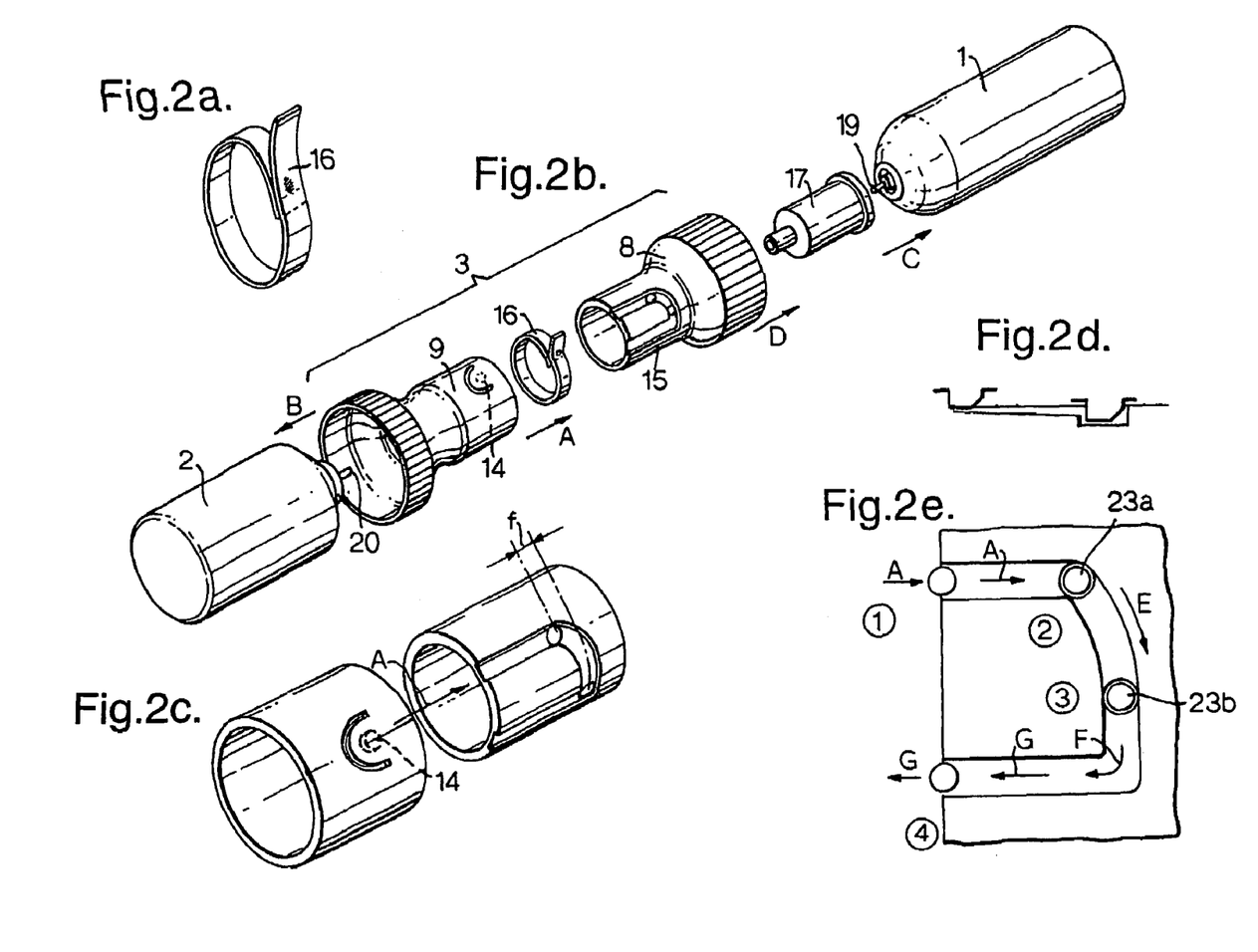
FIG. 2a shows the connector.
FIG. 2b shows the complete assembly.
FIG. 2c shows a cut-away portion of the connector.
FIG. 2d and FIG. 2e show cross-sections of the cam mechanism.

A further embodiment of the present invention is shown in FIG. 2, which is broadly similar in operation to Example 1, though incorporating a variant of the cam track mechanism. The device comprises a container (1) for an aqueous sclerosant liquid, a container (2) for a physiologically acceptable blood-dispersible gas and an engaging means comprising a connector (3). The two containers will again be referred to hereinafter as the PD [polidocanol] can (1) and the $O_2$ can (2).

The connector (3) is an assembly comprising a number of injection mouldings. It is made in two halves (8, 9), each provided with ribs to allow the user to grip and rotate the connector halves (8, 9) relative to each other. The two halves (8, 9) of the connector are in the form of cam track sleeves which fit together as two concentric tubes. These tubes are linked by a proud pin (14) on one half that engage a sunken cam track (15) on the other half. The cam track has two detented stop positions (23). The first of these detents (23a) is the stop position for storage following assembly. An extra security on this detent is given by placing a removable collar (16) in a gap between the end of one sleeve and the other. Until this collar (16) is removed it is not possible to rotate the sleeves past the first detent position. This ensures against accidental actuation of the connector. The removable collar (16) comprises a spacer in the form of an ultrasonically welded strip of plastics material, and until it is removed the pin (14) is held in a park position engaging the first stop (23a) of the detented cam track (15).

The cam track sleeves (8, 9) are injection moulded from ABS as separate items, comprising a cam collar (8) and a pin collar (9). The pin (14) is located on a resilient portion of the pin collar (9). They are later assembled by snapping together in the direction of arrow A so that the pin moves from position 1 in FIG. 2e to position 2, and the cam track sleeves (8, 9) engage one another on the first stop (23a) of the detented cam track (15). The assembled sleeves are snap-fitted as a unit onto the $O_2$ can (2) together in the direction of arrow B. The security collar is added at his point by ultrasonically welding it to the unit to make an $O_2$ can subassembly.

Figure 5A:
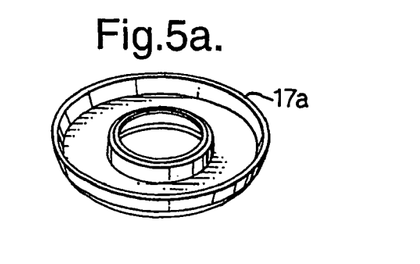
FIG. 5a shows the lid.
Figure 5B:
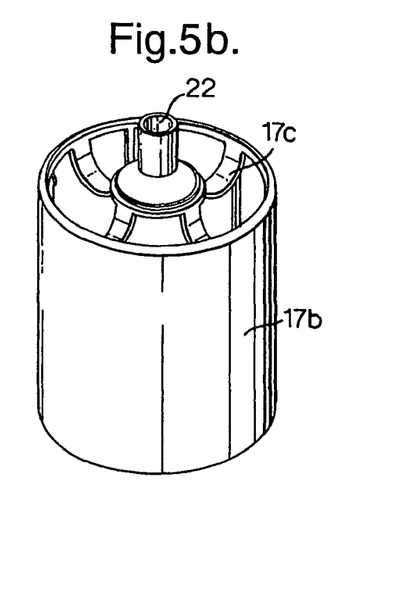
FIG. 5b shows the body and FIG. 5c shows the assembled secure actuator.
Figure 5C:
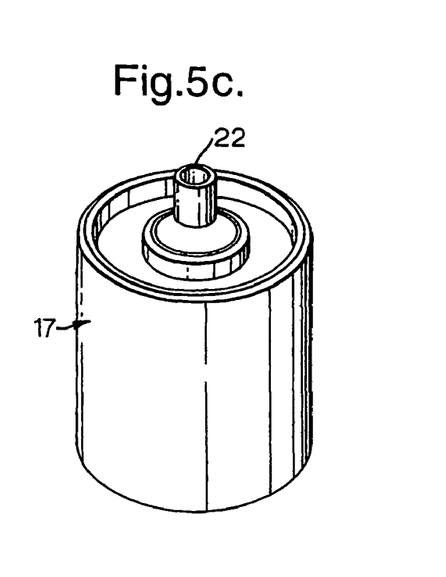

The connector (3) is designed to include on its interior a secure actuator (17) incorporating a mesh stack shuttle on the cam collar (8) adjacent to the PD can (1), as in Example 1. The secure actuator (17) is assembled onto the PD can valve (19) in the direction of arrow C, and is better shown in FIG. 5. It comprises a generally cylindrical frusto-conical body (17b) and an annular lid (17a). The a generally cylindrical body (17b) is connected to an outlet nozzle (22), sized to engage a luer fitting of a syringe or multi-way connector, by means of leaf springs (17c). The annular lid (17a) engages the open end of the generally cylindrical body (17b), so as to conceal the leaf springs (17c). Within the secure actuator is concealed the mesh stack shuttle (not shown).

The PD can (1) and attached secure actuator (17) are offered up to the connector (3) and the attached $O_2$ can (2), and a sliding fit made in the direction of arrow D. This completes the assembly of the system.

When the security collar (16) is removed, it is possible to grasp the ribs on the two connector halves (8, 9) and rotate one half of the connector (3) against the other half in the direction of arrow E, moving the pin (14) from its park position 2 engaging the first stop (23a) of the detented cam track (15) to an actuation position 3 engaging the second stop (23b) of the cam track (15). This causes the engagement and opening of the can valves (19, 20). The actual actuating stroke is the distance f.

After a 30 second wait at the actuation position 3, the connector (3) is rotated further by the user in the direction of arrow F. At this position, the two cans (1, 2) can be separated by moving the pin (14) to position 4 in FIG. 4e in the direction of arrow G and leaving the PD can (1) with half (8) of the connector and the shuttle assembly (17) captive between the connector and the PD can. The $O_2$ can (2) is discarded at this point.

Example 3

Figures 3A, 3B:
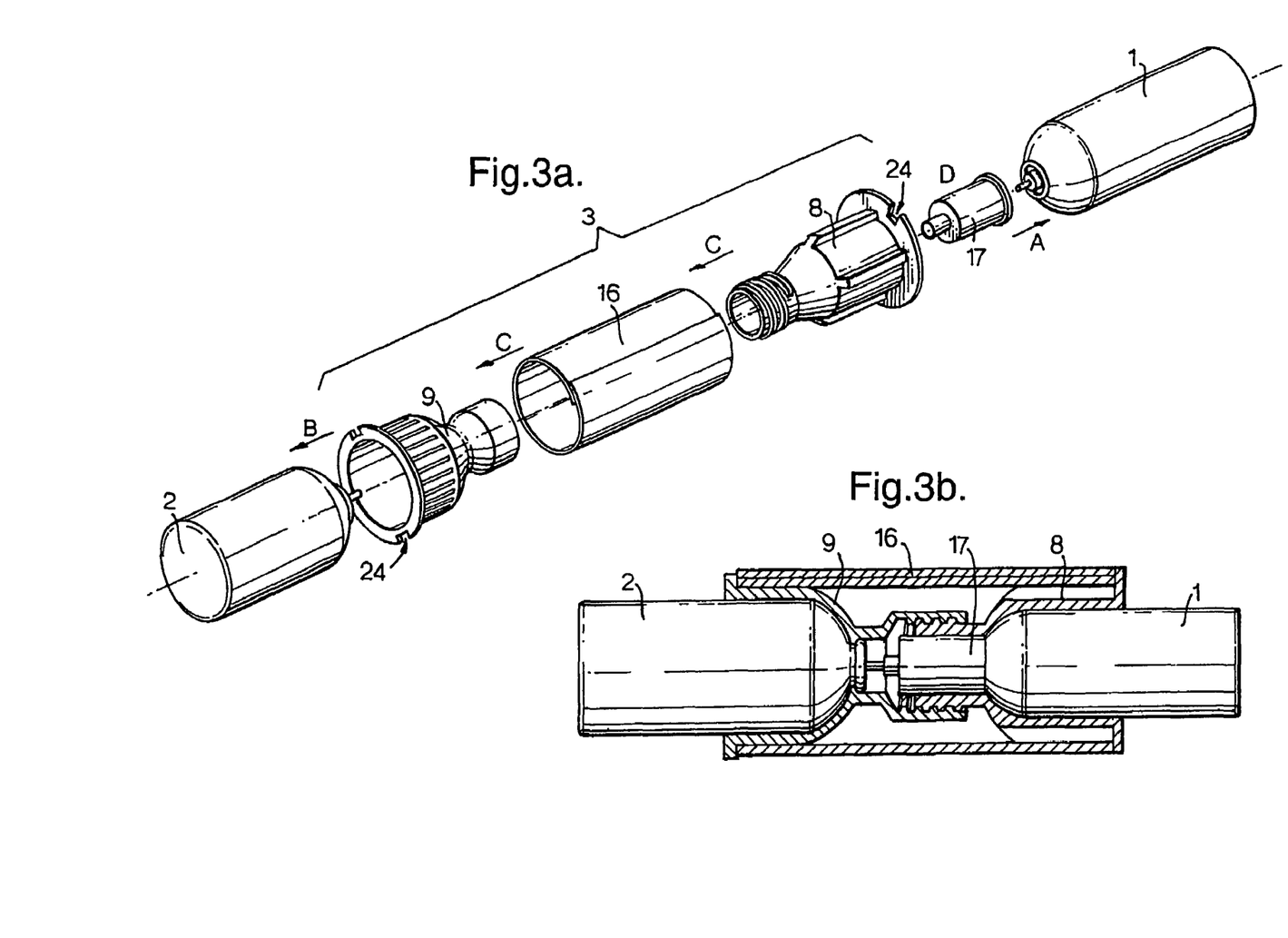
FIG. 3a shows the complete assembly
FIG. 3b shows a cross-section of the assembled device.

A further embodiment of the present invention incorporating a screw thread mechanism is shown in FIG. 3. The external form of the various elements is similar to Example 2. The device comprises a container (1) for an aqueous sclerosant liquid, a container (2) for a physiologically acceptable blood-dispersible gas and an engaging means comprising a connector (3). The two containers will again be referred to hereinafter as the PD [polidocanol] can (1) and the $O_2$ can (2).

The connector (3) is an assembly comprising a number of injection mouldings. It is made in two halves (8, 9), each provided with ribs to allow the user to grip and rotate the connector halves (8, 9) relative to each other. The injection-moulded halves (8, 9) comprise a male collar (8) and a female collar (9). An extra security is given by placing a removable collar (16) around the connector (3). The removable collar (16) comprises a spacer in the form of a cardboard tube. The two collars (8, 9) are each provided with drive tangs (24) to enable a corresponding tool to push them together in the direction of arrows C with the cardboard tube (16) applied The female collar (9) is snapped on to the $O_2$ can (2) in the direction of arrow B. The male collar (8) includes on its interior a secure actuator (17) incorporating a mesh stack shuttle as in Example 2. The secure actuator (17) is assembled onto the PD can valve (19) in the direction of arrow A, and the male collar (8) pushed over this in the direction of arrow D.

When the cardboard tube (16) is removed, it is possible to grasp the ribs on the two connector halves (8, 9) and rotate one half of the connector (3) against the other half in a clockwise direction. This causes the engagement and opening of the $O_2$ can valve and the PD can valve, as in Example 2.

After a 30 second wait, the two halves of the connector (3) are rotated in an anti-clockwise direction. The two cans (1, 2) can be separated and the $O_2$ can (2) discarded.

Example 4

A further embodiment of the present invention incorporating a snap mechanism is shown in FIG. 4. The external form of the various elements is similar to Example 3. The device comprises a container (1) for an aqueous sclerosant liquid, a container (2) for a physiologically acceptable blood-dispersible gas and an engaging means comprising a connector (3). The two containers will again be referred to hereinafter as the PD [polidocanol] can (1) and the $O_2$ can (2).

Figures 4A, 4B, 4C, 4D:
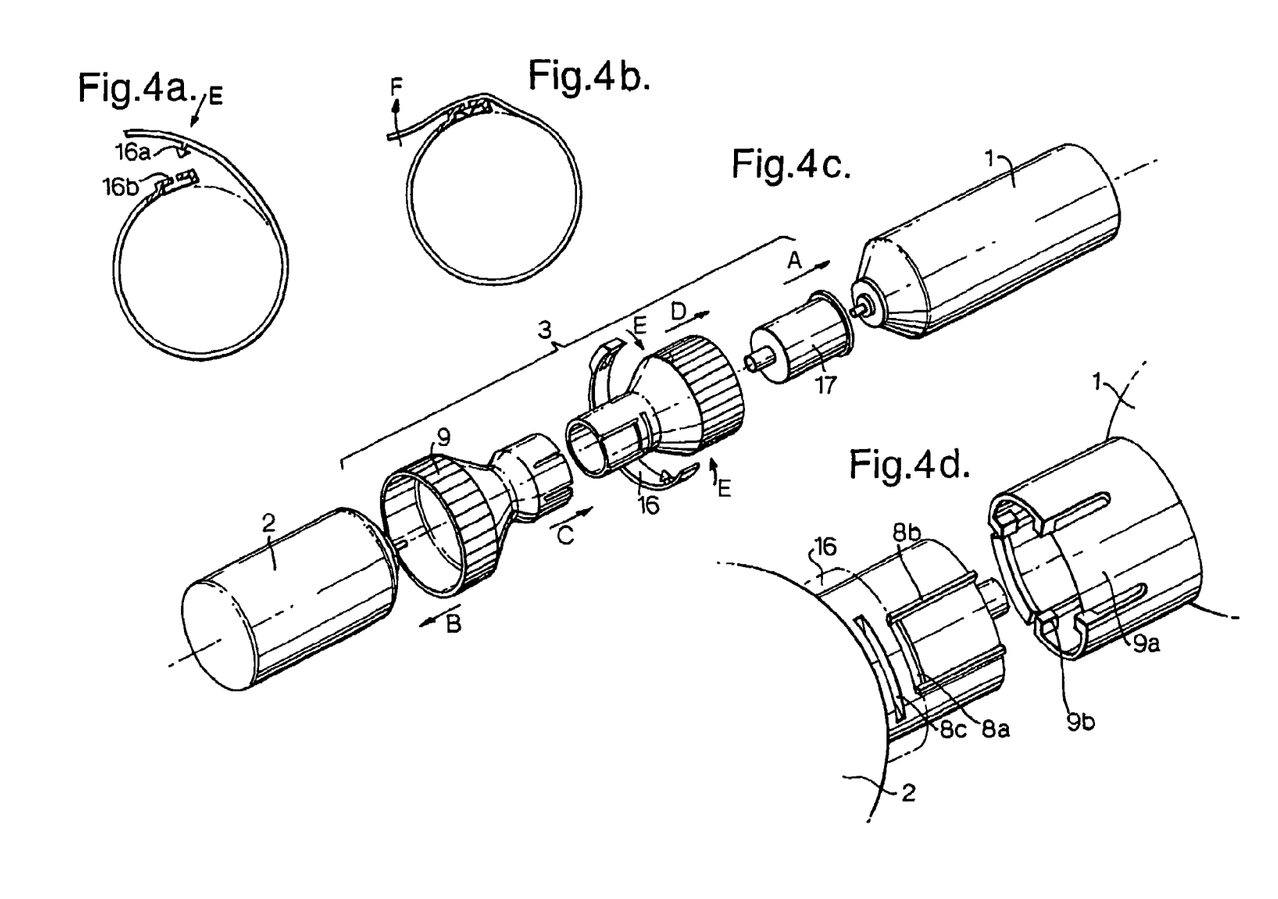
Figure 4E:
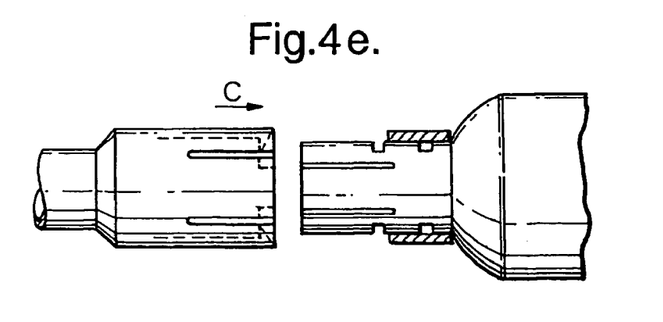
FIG. 4e, FIG. 4f, FIG. 4g and FIG. 4h show cross-sections of the snap mechanism.
Figure 4F:
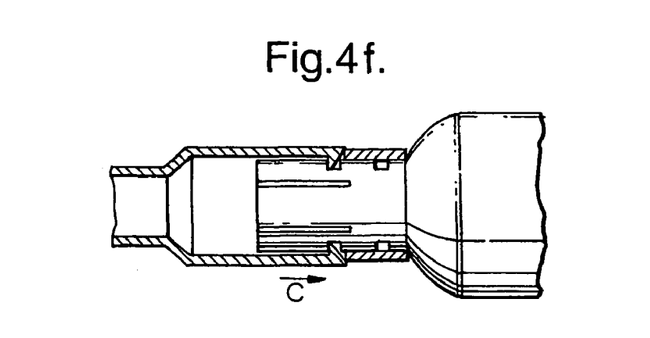

The connector (3) is an assembly and includes two injection-moulded halves (8, 9) comprising a male collar (8) and a female collar (9). An extra security is given by placing a removable collar (16). The removable collar (16) comprises a flexible spacer of plastics material including a resilient plug (16a) and socket (16b) which serve to lock the removable collar (16) in place by snapping in the direction of arrow E. The flexible spacer (16) may in addition be ultrasonically welded. The two injection-moulded halves (8, 9) are assembled by pushing them together in the direction of arrows C, as shown in FIGS. 4e and 4f, FIG. 4f showing the device in its transport position.

The female collar (9) is snapped on to the $O_2$ can (2) in the direction of arrow B. The male collar (8) includes on its interior a secure actuator (17) incorporating a mesh stack shuttle as in Example 2. The secure actuator (17) is assembled onto the PD can valve (19) in the direction of arrow A, and the male collar (8) pushed over this in the direction of arrow D.

The female collar (9) is made of resilient material and is provided with flexible teeth (9a) and tangs (9b). In the transport position, the teeth rest in corresponding grooves (8a) in the male collar (8). Additional grooves (8c) are provided adjacent to these, closer to the PD can (1). The tangs (9b) lock against corresponding ridges (8b) in the male collar (8).

Figure 4G:
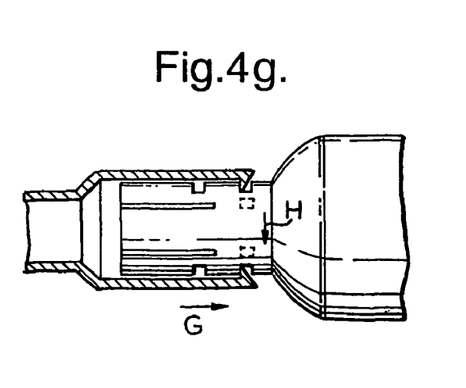
Figure 4H:
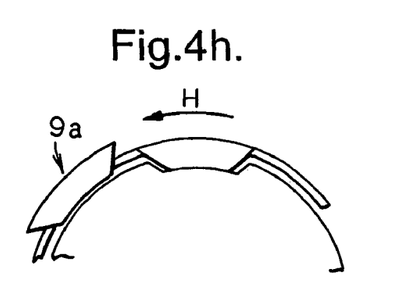

When the flexible spacer (16) is removed by pulling the resilient plug (16a) out of the socket (16b) in the direction of arrow F, it is possible to grasp the two cans (1, 2) and push one half of the connector (3) towards the other half in the direction of arrow G, as shown in FIG. 4g. The flexible teeth (9a) in the female collar (9) thereby move into the grooves (8c) closer to the PD can (1). This causes the engagement and opening of the $O_2$ can valve and the PD can valve, as in Example 2.

After a 30 second wait, the two halves of the connector (3) are rotated relative to each other in the direction of arrow H. This is possible as the tangs (9b) are now free of the ridges (8b) in the male collar (8). Rotation causes the flexible teeth (9a) in the female collar (9) to be disengaged. The two cans (1, 2) can be separated and the $O_2$ can (2) discarded.

The invention claimed is:

1. A device for producing a microfoam suitable for use in scleropathy of blood vessels, comprising: a housing in which is situated a pressurisable chamber containing a solution comprising at least one sclerosing agent in a physiologically acceptable solvent; a pathway with at least one outlet orifice by which the solution may pass from the pressurisable chamber to an exterior of the device through the at least one outlet orifice; and a mechanism by which the pathway from the pressurisable chamber to the exterior can be opened or closed such that, when the pressurisable chamber is pressurised and the pathway is open, fluid will be forced along the pathway and through the at least one outlet orifice; wherein the housing includes an inlet for the admission of a pressurised source of physiologically acceptable gas that is dispersible in blood, the physiologically acceptable gas being in contact with the solution upon activation of the mechanism to produce a gas-solution mixture, wherein the pathway to the exterior of the housing includes at least one foaming element, and wherein the physiologically acceptable gas that is dispersible in the blood is stored in a container provided with engaging means for engaging with the housing holding the solution comprising the at least one sclerosing agent and wherein the solution is stored in the presence of at least one inert gas.

2. The device as claimed in claim 1, wherein the at least one foaming element includes at least one passage having a cross sectional dimension of 0.1 μm to 30 μm, through which the gas-solution mixture is passed to reach the exterior of the device, the passing of the gas-solution mixture through the passage forms a microfoam ranging from 0.07 to 0.19 g/ml in density and having a half-life of at least 2 minutes.

3. The device as claimed in claim 1, wherein the pressurized source of physiologically acceptable gas is removed before the gas-solution mixture is released, having pressurised the gas-solution mixture to a pre-determined level before removal.

4. The device as claimed in claim 3, wherein the inlet for the admission of the physiologically acceptable gas includes the at least one outlet orifice for dispensing the gas-solution mixture.

5. The device as claimed in claim 1, wherein the engaging means includes an intermediate element.

6. The device as claimed in claim 5, wherein part of the intermediate element is removable before the gas-solution mixture is released, having pressurised the gas-solution mixture to a pre-determined level before removal.

7. The device as claimed in claim 5, wherein the intermediate element includes at least one foaming element to allow the components of the gas-solution mixture to interact to form the microfoam.

8. The device as claimed in claim 1, wherein the engaging means includes a connector, a first end of the connector being configured to engage with the housing and a second end of the connector being configured to engage with the container in which the pressurized source of physiologically acceptable gas is stored.

9. The device as claimed in claim 8, wherein the connector includes a substantially cylindrical element with open ends.

10. The device as claimed in claim 8, wherein the connector includes a cam track, whereby rotation of the containers relative to each other moves them together in a controlled fashion.

11. The device as claimed in claim 10, wherein the cam track is further provided with a release track for separating the containers again.

12. The device as claimed in claim 10, wherein at least one detent is provided in the cam track to gauge the progress of the introduction of the physiologically acceptable gas that is dispersible in the blood.

13. The device as claimed in claim 1, wherein a removable spacer is provided to prevent the container and the housing from being pushed together until required.

14. The device as claimed in claim 13, wherein the removable spacer takes the form of an annular collar positioned in between a connector in two parts.

15. The device as claimed in claim 8, wherein the connector includes an aerosol valve actuator mechanism, and wherein the container and the housing may be separated to leave the aerosol valve actuator mechanism attached to the housing.

16. A device for producing a microfoam suitable for use in scleropathy of blood vessels, comprising: a housing in which is situated a pressurisable chamber containing a solution comprising at least one sclerosing agent in a physiologically acceptable solvent; a pathway with at least one outlet orifice by which the solution may pass from the pressurisable chamber to an exterior of the device through the at least one outlet orifice; a mechanism by which the pathway from the pressurisable chamber to the exterior can be opened or closed such that, when the pressurisable chamber is pressurised and the pathway is open, fluid will be forced along the pathway and through the at least one outlet orifice; and a pressurised container containing a physiologically acceptable blood-dispersible gas; wherein the housing includes an inlet for the admission of the blood-dispersible gas, the gas being in contact with the solution upon activation of the mechanism to produce a gas-solution mixture and wherein the solution is stored in the presence of at least one inert gas.

17. The device as claimed in claim 16, wherein the pathway to the exterior of the housing includes at least one foaming element.

18. The device as claimed in claim 16, wherein the housing in which is situated the pressurisable chamber containing the solution of the sclerosing agent and the pressurized container containing the physiologically acceptable blood-dispersible gas are contained within a sealed package.

* * * * *